United States Patent [19]
Warren

[11] Patent Number: 5,792,384
[45] Date of Patent: Aug. 11, 1998

[54] CONCRETE MASONS' HAND RINSE

[76] Inventor: James R. Warren, 9306 Ravenswood, Grandbury, Tex. 76249

[21] Appl. No.: 792,450

[22] Filed: Jan. 31, 1997

[51] Int. Cl.$^6$ .................. A61K 7/40; A62D 3/00
[52] U.S. Cl. .................. 252/192; 252/1; 252/193; 424/604; 424/639; 510/100; 510/138; 510/159; 510/240; 106/740
[58] Field of Search .................. 252/192–193; 510/100, 131, 138, 159, 240, 407; 106/740, 739; 424/604, 639

[56] References Cited

U.S. PATENT DOCUMENTS

| | | | |
|---|---|---|---|
| 4,572,739 | 2/1986 | Rasmussen | 106/101 |
| 5,227,161 | 7/1993 | Kessler | 424/94.4 |
| 5,362,321 | 11/1994 | Larsen | 106/713 |

*Primary Examiner*—Joseph K. McKane
*Assistant Examiner*—Deanna Baxam
*Attorney, Agent, or Firm*—Guy V. Manning

[57] ABSTRACT

A buffer solution comprising one or more metal salts, preferably monobasic potassium phosphate and/or monosodium phosphate, dissolved in water creates a rinse having a pH near that of human skin. The buffer solution in various concentrations and compositions is adapted for routine use by professional and casual users of cement to rinse their skin and tools, as a spray-on application for skin and clothes, and as a pre-wash for laundry. The buffer solution may include other metal salts, preferably manganese sulfate, further to reduce hexavalent chromium carried into the rinse from cement. A pH color indicator such as phenolphthalein also may be included to signal when the buffer solution becomes ineffective from prolonged use.

17 Claims, No Drawings

CONCRETE MASONS' HAND RINSE

BACKGROUND OF THE INVENTION

1. Field of the Invention

This invention relates to improvements to skin cleaning agents, and particularly to such agents adapted to clean away residues of portland cement from concrete workers' skin. Still more particularly, this invention relates to a rinse for use by concrete workers to deter development of contact dermatitis from repeated or prolonged contact with wet portland cement.

2. Description of Related Art

Contact dermatitis produces a painful, eczemous, disabling reaction to irritants found in wet portland cement. Given time, wet concrete literally can dissolve human skin. The eczema manifests itself progressively as dryness, peeling, redness, inflammation, swelling, chapping, fissures, blisters and, ultimately, oozing sores. Understandably, professional concrete workers sometimes refer to the eczema as "concrete leprosy".

Two types occur. Irritant contact dermatitis results from excessive contact with detergents, solvents and alkaline materials such as portland cement and stucco. The eczema appears within hours of contact. In its acute, short term form, it is confined to affected areas having distinct borders. More incipient, the chronic form develops gradually, has indistinct borders and can persist for years after exposure. By contrast, allergic contact dermatitis occurs in response to small exposures to a substance after the worker has become sensitized to it. Both types may be present simultaneously.

Portland, or "hydrating," cement includes any cement which hardens when mixed with water. It comprises a mixture of limestone, silicates, aluminum, iron, magnesium, sand and fly ash. Soluble elements such as calcium hydroxide (CaOH) from the limestone elevate the alkalinity of the cement, which can reach a pH in excess of 12. Such elevated pH causes burns to skin as severe as acid burns. The worker often is unaware of the process, however, because it produces little or no heat. Where immediate injury does not occur, elevated pH often induces chronic irritant contact dermatitis. Means for reducing the pH of residue left on human skin after exposure to wet cement would considerably mitigate the long term detriments of such exposure.

Limestone and other rocks and minerals commonly used in cement production contain small amounts of chromium. Further, chrome alloy spheres used to pulverize the raw materials erode into the powdery product, called "clinker" in industry terms. Such chromium largely is insoluble in water at normal temperatures, but heating during manufacture of clinker oxidizes much of the chromium into water soluble hexavalent chromium ($Cr^{6+}$). Water liberates the hexavalent chromium when the cement is mixed to make concrete. Liquid portions of the wet cement then can penetrate clothing and skin to deposit the chromium contaminants into skin pores, leading to irritant contact dermatitis. Skin so exposed without relief can become sensitized to the presence of chromium, inducing allergic contact dermatitis. A need exists for an effective and inexpensive means for reducing worker exposure to hexavalent chromium and other soluble contaminants in wet cement.

Concrete workers often protect themselves during construction by wearing gloves, heavy clothes and rubber boots. Some contact with wet cement remains inevitable, however, at least by current standards of safety. Also, cement dust in the air can become deposited on skin, often into cracks and folds of skin where it concentrates. When the dust mixes with sweat, transfer of the solubles occurs. Residue left on tools also can re-contaminate a worker's skin when the tools later are handled, even after they dry. A need exists for further measures to mitigate the deleterious effects of daily exposure to such environmental workplace pollutants.

Common concrete work trade practices involve keeping a rinse bucket handy throughout the work day for periodically cleaning tools. The bucket serves not only to minimize water usage but also to trap cement residue. Workers commonly also rinse off their skin and clothes with water from the bucket. Such practice is particularly hazardous, because the wash water accumulates soluble portions of cement from previous washings, becoming increasingly alkaline and imbued with chromium, particularly hexavalent chromium. Even if workers towel off their skin after such rinse, the wash water leaves residue on their skin, including traces of hexavalent chromium which penetrates and accumulates in skin pores. A better practice uses fresh tap water for rinsing, but tap water often is not available on job sites, and if available, it does nothing to neutralize the pH or reduce chromium in residues left on the skin. A need exists for a rinse which reduces the high pH and chromium contamination from accumulated exposure to wet cement.

Efforts to counteract the effects of chromium and high pH in wet cement have been somewhat effective, but not without tradeoffs. Ferrous sulfate is known to reduce chromium in cement from the hexavalent stage to the trivalent stage, the latter of which readily precipitates. For example, in U.S. Pat. No. 4,784,691, Rasmussen discloses adding ferrous sulfate directly to portland cement during the manufacturing process. Though ferrous sulfate is inexpensive, it smells badly, is unpleasant to work with, produces large amounts of sludge and stains concrete and other materials. Jackson, U.S. Pat. No. 5,211,853, uses ammonia compounds to reduce hexavalent chromium from paper mill liquor for recycling and reducing waste products, but ammonia compounds are high in pH. Schreuder, U.S. Pat. No. 4,263,284, discloses a skin cleaning agent comprising a buffer of lactic acid and triethanolamine for maintaining normal pH of skin while other elements clean away cement, including chromium in pores. Schreuder proposes a complex mixture of some six phases, however, which is much too expensive for common industrial concrete construction practices. Lactic acid also is highly corrosive to steel, including rebar and concrete tools.

It also is known to use vinegar (acetic acid, $C_2H_4O_2$) or even the worker's own urine as pH reducing agents. The latter has obvious drawbacks, and the former has been shown to elevate the temperature of the wash bucket twenty (20) degrees or more very quickly. Acids, such as acetic or citric, may produce a low pH solution, but they do not create a stable buffer, because the pH rises rapidly when the solution is contaminated with cement.

SUMMARY OF THE INVENTION

Accordingly, it is an object of this invention to provide a rinse which lowers the pH on human skin after contact with cement.

It is another object of this invention to create a stable buffered solution which remains effective over sufficient time to be practicable to use on a construction job site for the intended effects described herein.

It is another object of this invention to provide a rinse for cleanup of concrete workers' tools which reduces residue of hexavalent chromium on such tools.

It is another object of this invention to provide a rinse which retards the amount of free hexavalent chromium absorbed by the skin of concrete workers.

The foregoing and other objects of this invention are achieved by providing a rinse comprising one or more metal salts, preferably monobasic potassium phosphate and/or monosodium phosphate, dissolved in water to create a buffer solution having a pH near that of human skin. The buffer solution in various concentrations and compositions is adapted for routine use by professional and casual users of cement to rinse their skin and tools, as a spray-on application for skin and clothes, and as a pre-wash for laundry. The buffer solution may include other metal salts, preferably manganese sulfate, further to reduce hexavalent chromium carried into the rinse from cement. A pH color indicator such as phenolphthalein also may be included to signal when the buffer solution becomes ineffective from prolonged use.

DESCRIPTION OF PREFERRED EMBODIMENTS

It has been discovered that a buffered rinse substantially lowers the pH of residue left on concrete workers' skin. The present invention comprises a stable, buffered rinse to be used after exposure to concrete, both for tools and for human skin and clothing. The rinse preferably comprises a solution of monobasic potassium phosphate ($KH_2PO_4$) in concentrations ranging from ½% to 20%, preferably 1½% by weight. Such preferred concentration translates to two (2 oz.) ounces of dry granules of the compound per gallon of water. The rinse maintains its buffering effect long enough to be useful on a construction job site.

A buffer solution of monobasic potassium phosphate is preferred for professional concrete workers because of its additional ability, illustrated by the examples below, to reduce amounts of hexavalent chromium. To boost the effectiveness of the buffer solution, other metal salts, preferably manganese sulfate ($MnSO_4$), may be added to help to convert hexavalent chromium to trivalent chromium ($Cr^{3+}$). See Klemm, W. A., "Hexavalent Chromium in Portland Cement," *Cement, Concrete, and Aggregates*, CCAGPD, Vol. 16, No. 1, June, 1994, pp. 43–47, incorporated herein by reference. Trivalent chromium is less soluble than hexavalent chromium and more readily precipitates, leaving the rinse with less overall dissolved chromium to be deposited as residue on skin, clothing and tools.

For casual users, such as homeowners who purchase dry, mixed concrete in bags at local hardware stores, less expensive monosodium phosphate ($Na_2H_2PO_4$) is preferred because of lower cost. Though monosodium phosphate is highly effective in reducing pH, its effects on hexavalent chromium are uncertain. Casual users, however, are much less likely than professional concrete workers to receive enough exposure to hexavalent chromium to contract allergic dermatitis. A pH buffer is even more important for casual users, however. They are less likely to be aware of the dangers of wet concrete, and thus less likely to take adequate precautions, making them more vulnerable to acute irritant dermatitis than are professional concrete workers.

The buffer solution of the present invention is not a detergent, but a neutral or slightly acidic rinse for mitigating the hazards of residue left on workers' skin from contact with wet portland cement, particularly the water soluble portions such as calcium hydroxide (CaOH) and hexavalent chromium. In fact, addition of a surfactant or a wetting agent could produce undesirable results. Surfactants can penetrate and render ineffective the top skin layers which contain protective natural oils, thus encouraging absorption by the skin of dissolved contaminants from the wash water.

As the buffer solution is used, its pH increases with increasing amounts of cement residue rinsed off of tools and skin and into the water. A bucket of the rinse continues to function as designed until its pH rises to near the pH level of the cement itself. As the examples below indicate, the present invention resists this increase for useful durations. To elevate the buffer solution to a pH of 11.0, it requires a pound (16 oz.) of cement per gallon of water at a one and one-half (1½%) percent concentration (Example 1), and almost five (5) pounds (75 oz.) for a seven and one-half (7½%) percent concentration (Example 3). Such contamination is far more than would be expected during a single day at a construction job site. Nevertheless, if used long enough, the buffer solution of the present invention eventually becomes ineffective for reducing pH, though it may remain effective for chromium.

To determine when the buffer pH becomes too high, a pH color indicator such as phenolphthalein ($C_{20}H_{14}O_4$) may be included in concentration sufficient to cause it to change color without ambiguity when the solution reaches the threshold pH of about 10. A convenient concentration of phenolphthalein comprises one milligram of phenolphthalein per milliliter (1 mg/mL) of ethanol in a concentration of two milliliters (2 mL/gallon) per gallon of buffer solution. When the pH of the rinse approaches 10, the rinse changes to a pink color, easily recognizable as indicating it needs to be replaced. One having ordinary skill in the art will recognize that other pH indicators could be used without departing from the spirit and scope of the present invention.

The buffered solution also may be packaged in a spray bottle for spray application directly to clothing and skin. In this embodiment, concentrations of one and one-half to seven and one-half (1½–7½%) percent, preferably seven and one-half (7½%) percent, are used for localized and more rapid neutralizing effect. For example, a worker may spill liquids from concrete onto himself at places which he does not wish to or cannot immerse into the wash bucket (such as inside his shoes). Some evidence suggests that a residue of the rinse also provides a short term barrier to contaminants.

For clothing, which often is worn home even though having been saturated with contaminated water, an effective way of neutralizing the pH is to spray some of the buffer solution directly onto saturated parts of clothing. In similar manner, the spray may serve as a pre-wash for laundry further to neutralize pH and to convert hexavalent chromium during laundering of contaminated clothing. In the laundry context, surfactants and detergents in the laundry are not of concern because the worker's skin is not exposed to the laundry water.

EXAMPLES

The following examples further describe the present invention by way of additional detail and test results. These examples in no way limit the scope of the invention.

Example 1

A solution of rinse treatment was prepared using two (2 oz.) ounces of monobasic potassium phosphate to a gallon of water. A control treatment of plain water also was prepared. The pH of both treatments was measured. Then, three one-fourth (¼ oz.) ounce additions of portland cement (CTL lab blend 221108) were added to the control until its pH exceeded 11. To both treatments then were added sixteen (16) one (1 oz.) ounce additions of cement at fifteen (15) minute intervals for the next four hours. The pH of the treatments was measured after one minute of mixing each of the additions. A final addition of ¾ oz. of cement was added to the buffered treatment to match the amount of cement added to the control. After the additions were completed, the solutions were filtered through a fiber glass filter and hexavalent chromium was measured by standard addition analysis with diphenylcarbazide using a Cary 3 Uv-vis spectrophotometer. Hexavalent chromium was determined following a modified Method 7196 from "Test Methods for Evaluating Solid Waste", EPA Office of Solid Wastes, 2nd. ed. July 1982.

|  | Control | | Treatment | |
| --- | --- | --- | --- | --- |
|  | pH | $Cr^{6+}$ (mg/L) | pH | $Cr^{6+}$ (mg/L) |
| Initial | 7.02 |  | 7.10 |  |
| Buffer added | X |  | 5.26 |  |
| Cement added (1 oz.) | X |  | 5.93 |  |
| Cement added (¼ oz.) |  |  |  |  |
| 1 | 10.59 |  | X |  |
| 2 | 10.91 |  | X |  |
| 3 | 11.10 |  | X |  |
| Cement added (1 oz.) |  |  |  |  |
| 1 | 11.02 |  | 6.69 |  |
| 2 | 11.14 |  | 7.23 |  |
| 3 | 11.14 |  | 7.91 |  |
| 4 | 11.25 |  | 8.36 |  |
| 6 | 11.40 |  | 8.84 |  |
| 7 | 11.20 |  | 9.27 |  |
| 8 | 11.12 |  | 9.41 |  |
| 9 | 11.07 |  | 9.50 |  |
| 10 | 11.15 |  | 9.59 |  |
| 11 | 11.24 |  | 9.78 |  |
| 12 | 11.27 |  | 9.91 |  |
| 13 | 11.28 |  | 10.02 |  |
| 14 | 11.44 |  | 10.25 |  |
| 15 | 11.42 |  | 10.43 |  |
| 16 | 11.52 |  | 10.57 |  |
| Cement added (¾ oz.) | X | 0.51 | 10.68 | 0.23 |

X = nothing added

As the data indicate, the effect on pH of the buffered treatment is substantially linear over the test range, and attenuated in each instance relative to the control (no buffer). A surprise result appears for the hexavalent chromium in solution, which is depressed by over fifty (50%) percent relative to the control.

Example 2

The procedure described for the previous example was followed for a buffer comprising one and one-third (1.33 oz.) ounces of monobasic potassium phosphate combined with two-thirds (0.66 oz.) ounce of manganese sulfate as an additional treatment for hexavalent chromium ($Cr^{6+}$).

|  | Control | | Treatment | |
| --- | --- | --- | --- | --- |
|  | pH | $Cr^{6+}$ (mg/L) | pH | $Cr^{6+}$ (mg/L) |
| Initial | 7.02 |  | 7.08 |  |
| Buffer added | X |  | 4.72 |  |
| Cement added (1 oz.) | X |  | 4.98 |  |
| Cement added (¼ oz.) |  |  |  |  |
| 1 | 10.59 |  | X |  |
| 2 | 10.91 |  | X |  |
| 3 | 11.10 |  | X |  |
| Cement added (1 oz.) |  |  |  |  |
| 1 | 11.02 |  | 5.03 |  |
| 2 | 11.14 |  | 5.02 |  |
| 3 | 11.14 |  | 5.17 |  |
| 4 | 11.25 |  | 5.39 |  |
| 6 | 11.40 |  | 5.71 |  |

-continued

|  | Control | | Treatment | |
| --- | --- | --- | --- | --- |
|  | pH | $Cr^{6+}$ (mg/L) | pH | $Cr^{6+}$ (mg/L) |
| 7 | 11.20 |  | 5.75 |  |
| 8 | 11.12 |  | 6.08 |  |
| 9 | 11.07 |  | 6.43 |  |
| 10 | 11.15 |  | 6.81 |  |
| 11 | 11.24 |  | 7.27 |  |
| 12 | 11.27 |  | 8.11 |  |
| 13 | 11.28 |  | 11.08 |  |
| 14 | 11.44 |  | 11.50 |  |
| 15 | 11.42 |  | 11.65 |  |
| 16 | 11.52 |  | 11.78 |  |
| Cement added (¾ oz.) | X | 0.51 | 11.82 | 0.23 |

X = nothing added

Unlike in the previous example, the pH effect of the buffer with the manganese sulfate is non-linear, a sudden jump in pH occurring upon addition of the thirteenth ounce increment. The additional benefit of the manganese sulfate also did not translate into improved deterrence of hexavalent chromium, as anticipated by the literature. The addition of manganese sulfate did, however, improve the early pH suppression in contrast to the first example, up to a certain point.

Example 3

To test the effect of time on pH, simulating changes in a rinse bucket used for several hours, ten (10 oz.) ounces of monosodium phosphate ($NaH_2PO_4$) was added to a gallon of tap water to create a seven and one-half (7½%) percent solution of buffer solution. Raw cement was added in three (3 oz.) ounce increments at five (5) minute intervals for two and one half (2½hr.) hours, and the pH measured after each addition. Chromium levels were not studied.

|  | Cement (Cumulative) oz. | Treatment pH |
| --- | --- | --- |
| Initial |  | 8.7 |
| Buffer added |  | 4.4 |
| Cement added (3 oz.) |  |  |
| 1 | 3.0 | — |
| 2 | 6.0 | 5.1 |
| 3 | 9.0 | 5.3 |
| 4 | 12.0 | 5.6 |
| 5 | 15.0 | 6.4 |
| 6 | 18.0 | 6.6 |
| 7 | 21.0 | 7.2 |
| 8 | 24.0 | 7.7 |
| 9 | 27.0 | 8.2 |
| 10 | 30.0 | 8.6 |
| 11 | 33.0 | 9.1 |
| 12 | 36.0 | 9.4 |
| 13 | 39.0 | 9.6 |
| 14 | 42.0 | 9.8 |
| 15 | 45.0 | 9.9 |
| 16 | 48.0 | 10.1 |
| 17 | 51.0 | 10.2 |
| 18 | 54.0 | 10.4 |
| 19 | 57.0 | 10.4 |
| 20 | 60.0 | 10.5 |
| 21 | 63.0 | 10.6 |
| 22 | 66.0 | 10.7 |
| 23 | 69.0 | 10.8 |
| 24 | 72.0 | 10.9 |
| 25 | 75.0 | 11.0 |
| Cement added (0.0 oz.) |  |  |
| 26 | 75.0 | 11.1 |

-continued

|    | Cement (Cumulative) oz. | Treatment pH |
|----|-------------------------|--------------|
| 27 | 75.0                    | 11.1         |
| 28 | 75.0                    | 11.2         |
| 29 | 75.0                    | 11.2         |

A slight temperature rise was detected at increment 6. Phenolphthalein was added at increment 13, and a slight pink color appeared. Addition of cement ceased upon reaching a pH of 11.0, and measurements were repeated for another 20 minutes with only insignificant changes in pH.

It has been suggested that uptake of hexavalent chromium in the rinse water may be exacerbated by the slightly acidic nature of the buffer itself. The buffer's starting pH was selected for the present invention to fall within the range of 7.0 to 5.0, preferably to be near that of human skin at 5.5. A lower pH would cause stinging of minor cuts or other open sores on a worker's skin, just as juice from an orange (pH of about 4.1) can do. Also, water varies considerably in its pH, which can affect the starting pH of the rinse. Therefore, addition of another metal salt, such as disodium phosphate (pH of about 8.0) could serve to adjust the starting pH of the buffer rinse if need be.

Example 4

The procedure described for Example 1 was followed without control for a buffer comprising a 50/50 mix of monobasic potassium phosphate and disodium phosphate in concentration of 2.2 grams per 300 milliliters (300 mL) of water. For each measurement, portland cement was added to the water and stirred in increments of 0.8 grams until the pH measured 11 or higher. At that point, the total chromium content (including hexavalent chromium and other forms) was measured and reported.

|                      | Treatment pH (mg/L) | $Cr^{6+}$ |
|----------------------|---------------------|-----------|
| Buffer added         | 7.65                |           |
| Cement added (0.8 gm)|                     |           |
| 1                    | 7.75                |           |
| 2                    | 7.92                |           |
| 3                    | 8.30                |           |
| 4                    | 8.45                |           |
| 5                    | 8.63                |           |
| 6                    | 8.75                |           |
| 7                    | 8.85                |           |
| 8                    | 8.95                |           |
| 9                    | 9.13                |           |
| 10                   | 9.38                |           |
| 11                   | 9.73                |           |
| 12                   | 10.00               |           |
| 13                   | 10.18               |           |
| 14                   | 10.32               |           |
| 15                   | 10.49               |           |
| 16                   | 10.61               |           |
| 17                   | 10.84               |           |
| 18                   | 11.02               | 0.07      |

Even though the addition of disodium phosphate elevated the starting pH of the buffer solution, it remained stable through the addition of the equivalent of approximately 0.4 pound of cement into a gallon of water. The major gain illustrated is the low residual of total chromium, which was reduced proportionately lower than residuals of hexavalent chromium alone in Examples 1 and 2.

The foregoing examples and discussion illustrate that the buffered solutions retard increase of pH in a wash bucket increasingly contaminated with raw cement. This suggests that the present invention could serve as an initial wash for tools and skin, as well as a final rinse stage. When additionally buffered by manganese sulfate, a non-linear suppression enhances the benefit of the phosphate salt. A color pH indicator which triggers at specified pH to notify workers that the rinse has become ineffective for counteracting alkalinity should trigger at a pH of about 10. No additional rise in pH with time passage or increase in ambient temperature was observed, alleviating concern that a bucket of the rinse can become more hazardous by just standing throughout the day at a job site.

While the invention has been particularly shown and described with reference to a preferred embodiment, it will be understood by those skilled in the art that various changes in form and detail may be made therein without departing from the spirit and scope of the invention.

I claim:

1. A buffered rinse for reducing alkalinity and chromium contamination of residues from wet cement on concrete workers' skin and tools consisting of at least one metal salt selected from the group consisting of monosodium phosphate, disodium phosphate and potassium monobasic phosphate dissolved in water at concentrations of ½ percent to 20 percent by weight, and a color pH indicator; the rinse having an effective resulting pH in the range of 7.0 to 4.0; and wherein said amount of metal salt is effective to reduce the development of contact dermatitis when the buffered rinse is exposed to human skin.

2. The buffered rinse according to claim 1 wherein the compound selection comprises
   potassium monobasic phosphate.

3. The buffered rinse according to claim 2 wherein
   the potassium monobasic phosphate is provided in a concentration of 1½ percent by weight.

4. The buffered rinse according to claim 2 wherein
   the potassium monobasic phosphate is provided at a concentration of 7½ percent by weight.

5. The buffered rinse according to claim 2 and further comprising manganese sulfate.

6. The buffered rinse according to claim 5 wherein
   the potassium monobasic phosphate is provided in a concentration of 1 percent by weight; and
   the manganese sulfate is provided in concentration of one-half ½ percent by weight.

7. The buffered rinse according to claim 1 wherein the compound selection comprises
   monosodium phosphate.

8. The buffered rinse according to claim 7 wherein
   the monosodium phosphate is provided at a concentration of 7½ percent by weight.

9. The buffered rinse according to claim 8 and further
   provided in spray bottle packaging adapted for direct application to isolated sites on the skin and clothing.

10. The buffered rinse according to claim 2 and further comprising
    disodium phosphate.

11. The buffered rinse according to claim 10 wherein the color pH indicator comprises
    phenolphthalein.

12. A method of retarding development of contact dermatitis in concrete workers comprising
    providing a buffered rinse comprising at least one compound from a group of metal salts consisting of monosodium phosphate, disodium phosphate and potassium monobasic phosphate dissolved in water wherein the pH of the resulting rinse falls in the range of 7.0 to 4.0;

providing a container of the buffered rinse having a concentration of 1½ percent by weight on a job site for a second stage rinse after use of a wash of plain water for tools and skin;

providing a spray container of the buffered rinse having a concentration of 7½ percent by weight on a job site for a final stage rinse; then rinsing concrete workers' skin and tools in plain water; then rinsing the concrete workers' skin and tools in the second stage buffered rinse after exposure to wet cement; then spraying as needed for thorough protection isolated portions of workers' skin and clothing with the final stage rinse; and allowing the buffered rinse to dry on the skin and tools.

13. The method of claim 12 and further comprising the steps of providing a color pH indicator in the second stage buffered rinse;

periodically monitoring the color of the second stage buffered rinse; and replacing the second stage buffered rinse when the color pH indicator indicates that the rinse has reached a predetermined alkalinity.

14. A buffered rinse for reducing alkalinity and chromium contamination of residues from wet cement on concrete workers' skin and tools consisting of potassium monobasic phosphate dissolved in water at concentrations of ½ percent to 20 percent by weight, and a color pH indicator; the rinse having an effective resulting pH in the range of 7.0 to 4.0; and wherein said amount of potassium monobasic phosphate is effective to reduce the development of contact dermatitis when the buffered rinse is exposed to human skin.

15. The buffered rinse according to claim 14 further comprising manganese sulfate.

16. The buffered rinse according to claim 15 wherein the potassium monobasic phosphate is provided in a concentration of one 1 percent by weight; and the manganese sulfate is provided in concentration of one-half ½ percent by weight.

17. The buffered rinse according to claim 14 further comprising disodium phosphate.

* * * * *